United States Patent [19]
Tomita et al.

[11] Patent Number: 5,340,924
[45] Date of Patent: Aug. 23, 1994

[54] METHOD FOR HEAT TREATMENT OF LACTOFERRIN WITHOUT LOSING PHYSIOLOGICAL ACTIVITIES THEREOF

[75] Inventors: Mamoru Tomita; Yoshitaka Tamura, both of Yokohama; Hiroshi Miyakawa, Kamakura; Hitoshi Saito, Kawasaki; Hiroaki Abe, Yokosuka; Eiji Nagao, Sagamihara, all of Japan

[73] Assignee: Morinaga Milk Industry Co., Ltd., Tokyo, Japan

[21] Appl. No.: 860,224

[22] Filed: Mar. 27, 1992

Related U.S. Application Data

[63] Continuation-in-part of Ser. No. 603,416, Oct. 26, 1990, abandoned.

[30] Foreign Application Priority Data

Jan. 18, 1990 [JP] Japan ................................. 2-10266

[51] Int. Cl.$^5$ .................. C07K 3/12; C07K 15/00; C07K 15/14; C07K 15/22
[52] U.S. Cl. ................................. 530/395; 530/400; 530/427; 530/832
[58] Field of Search ............... 530/395, 400, 427, 832

[56] References Cited

U.S. PATENT DOCUMENTS

| | | | |
|---|---|---|---|
| 2,602,747 | 7/1952 | Meade | 530/427 |
| 4,259,356 | 3/1981 | Wallgreen et al. | 530/832 |
| 4,791,193 | 12/1988 | Okonogi et al. | 530/382 |
| 5,008,120 | 4/1991 | Tanaka et al. | 426/590 |
| 5,116,953 | 5/1992 | Dosako et al. | 426/522 |

*Primary Examiner*—Jeffrey E. Russel
*Attorney, Agent, or Firm*—Oblon, Spivak, McClelland, Maier & Neustadt

[57] ABSTRACT

A method for treatment of a matter which contains moisturized or liquified lactoferrin which has been isolated from mammalian milk, processed mammalian milk and by-products in mammalian milk-processing, without losing the physiological activities of lactoferrin, which comprises adjusting pH of said moisturized or liquefied lactoferrin contained in said matter within an acidic range between 2.0 and 6.0 both inclusive by adding acid or aqueous solution of acid when the pH of said moisturized or liquefied lactoferrin is out of said pH range, and heating said matter in the range from 60° C. to 130° C. for a span of time which may assure 60% or more of undenaturization rate of lactoferrin.

2 Claims, 1 Drawing Sheet

5,340,924

METHOD FOR HEAT TREATMENT OF LACTOFERRIN WITHOUT LOSING PHYSIOLOGICAL ACTIVITIES THEREOF

This application is a continuation-in-part of application Ser. No. 07/603,416, filed on Oct. 26, 1990, now abandoned.

FIELD OF THE INVENTION

The present invention relates to a method for heat treatment of lactoferrin or matters containing lactoferrin without losing physiological activities thereof. More particularly, the present invention relates to a method for heat treatment of lactoferrin or matters containing lactoferrin under a pH condition between 1.0–6.5 at a temperature over 60° C.

BACKGROUND OF THE INVENTION

Lactoferrin is known as an iron-binding protein distributed in tear, saliva, peripheral blood, milk and the like. It has been known that lactoferrin has various physiological activities, for example, antibacterial activity against harmful bacteria (B. J. Nonnecke, and K. L. Smith; Journal of Dairy Science; Vol. 67, p. 3; 1984), activity for promoting iron absorption by the intestine (G. B. Fransson et al; Journal of Pediatric Gastroenterology and Nutrition; Vol. 2, p. 693; 1983), anti-flammatory activity (J. V. Bannister et al; Biochimica et Biophysica Acta; Vol. 715, p. 116; 1982) and so on.

Therefore addition of lactoferrin to foods, processed foods, medicines, cosmetics and the like is desirable.

However, lactoferrin is unstable to heating at near neutral pH, and heat treatment of lactoferrin may result in denaturation of lactoferrin. It is reported that the physiological activities of lactoferrin are almost lost by heating at 62.5° C. for 30 minutes, and complete denaturation is achieved by heating at 70° C. for 15 minutes (J. E. Ford et al; Journal of Pediatrics, Vol. 90, page 29; 1977). In this connection, a typical condition of traditional thermal sterilization of milk is heating at 63° C. for 30 minutes.

It is often necessary to heat foods, feeds, medicines and cosmetics for pasteurization, sterilization, or cooking, however, sufficient thermal treatment could not be applied to lactoferrin or matters containing lactoferrin as an ingredient for utilizing its physiological activities.

The inventors of the present invention have exerted their efforts to develop a method for heat treatment of lactoferrin or matters containing lactoferrin without losing its physiological activities, and have found that when lactoferrin or matters containing lactoferrin are heated under acidic conditions, its physiological activities such as antibacterial activity, iron-binding activity and antigenicity are scarcely affected. This invention is based on this discovery.

OBJECTS OF THE INVENTION

Therefore, it is an object of the present invention to provide a method for heat treatment of lactoferrin or matters containing lactoferrin without losing the physiological activities thereof.

It is a particular object of the present invention to provide a method for pasteurization, sterilization or cooking by heating of lactoferrin or matters containing lactoferrin without losing the physiological activities thereof.

SUMMARY OF THE INVENTION

In accordance with the present invention, lactoferrin or matters containing lactoferrin are heated at a temperature over 60° C. under a pH condition between 1.0–6.5.

DETAILED DESCRIPTION OF THE INVENTION

Figure 1:
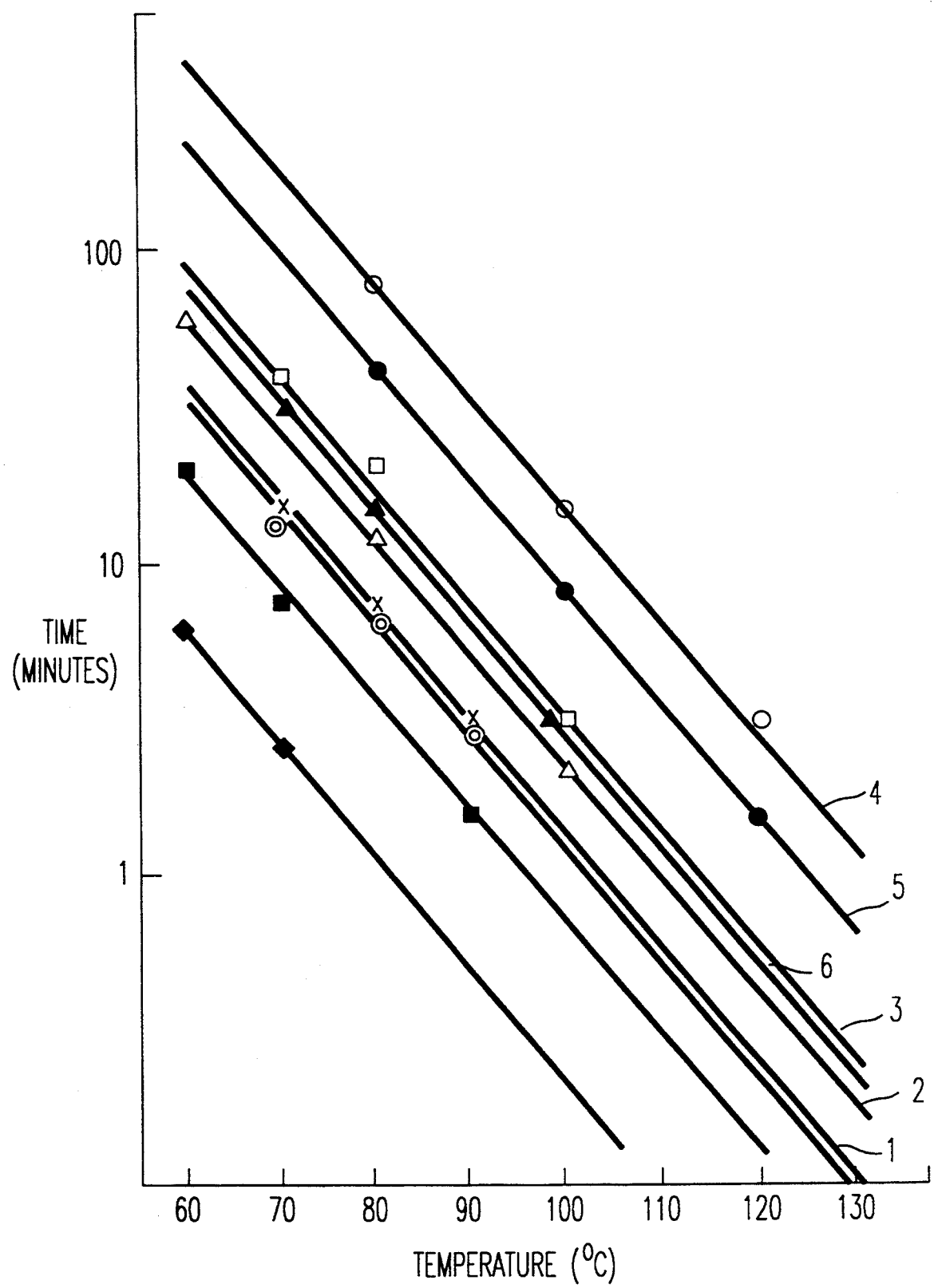
FIG. 1 is a graph showing relationships between heating temperature and heating time with respect to lactoferrin samples having different pH values for assuring undenaturation rates over 60%.

The word "lactoferrin" used herein includes lactoferrin derived from any and all sources of lactoferrin such as mammalian milk (for example, human milk as well as cow's, sheep's, goat's, horse's milk and the like) at any lactation stage (for example, colostrum, transitional milk, matured milk, milk in later lactation), processed milk and byproducts in milk-processing such as skim milk, whey and the like (hereinafter they are referred to in general as milk and the like).

The word "lactoferrin" used herein include any and all lactoferrin substances, such as: commercial lactoferrin; native lactoferrin just isolated by the conventional method (for example, ion-exchange chromatography) from any and all sources of lactoferrin; apolactoferrin obtained by removing iron from native lactoferrin with hydrochloric acid, citric acid and the like; metal saturated lactoferrin obtained by chelating apolactoferrin with a metal such as iron, copper, zinc, manganese and the like; or suitable mixtures thereof (hereinafter they are abbreviated as LF in general).

The words "matters containing lactoferrin" used herein include any and all matters which inherently contain LF, and any and all matters to which LF is added. For example, matters containing lactoferrin may include foods, feeds, cosmetics and medicines and the like which include LF. For the sake of simplicity, lactoferrin and matters containing lactoferrin will be referred to hereinafter as LF-matters in general.

Typically, heat treatment of LF-matters is performed in liquid phase, however, LF-matters are not necessarily in liquid phase, but the matters must contain lactoferrin in a state or a phase wherein LF is placed under a pH condition within the described range. For example, LF-matters may include coarse solid matters wherein LF is mixed or stuck in a form of liquid, slurry or paste.

In accordance with the method of the present invention, LF-matters first have their pH adjusted to within the range 1.0–6.5, preferably 2.0–6.0 by adding inorganic acid (for example, hydrochloric acid, phosphoric acid and the like) and/or organic acid (for example, acetic acid, citric acid and the like). Certainly, when LF-matters, per se, have a pH value within the described range, pH adjustment is unnecessary, however, it is still preferable to adjust the pH of LF-matters to the optimum pH depending upon the heating condition to be adopted (heating temperature and heating time) and the purpose of heating (for example, sterilization, cooking and the like).

The pH range was determined as the results of Test 1 which shows that an LF solution tend to coagulate by heating in the pH range between 6.5–10.0 and tend to be hydrolyzed by heating at a pH value over 10.0 or below 1.0, however, denaturation or hydrolysis of LF can be minimized when it is heated at a temperature higher than 60° C. in the pH range between 1.0–6.5 for a relatively short time.

In accordance with the present invention, heat treatment is made at a temperature over 60° C. The temperature range of heat treatment is mainly intended for sterilization, but it was determined taking practical heat processing in the food industry into consideration. Heating of LF-matters may result, more or less, in the denaturation of LF and may affect the physiological activities thereof. Potency of physiological activities of LF generally depend upon concentration of LF. Thus, in order to utilize physiological activities of LF, it is desirable to include undenaturated LF as much as possible in the heated LF-matters. From the practical point of view, undenaturation rate of LF in LF-matters is set as more than 60% in the present invention, though it is not critical. The words "undenaturation rate" used herein means the rate of the quantity of undenaturated LF in the LF-matters after heating to that before heating.

In conclusion, heat treatment of LF-matters is performed at a pH of 1.0–6.5 with a proper combination of a temperature over 60° C. and a proper span of time to achieve an undenaturation rate over 60%.

LF-matters treated by heating are cooled by conventional methods, if necessary, filled in containers and sealed, to thereby obtain LF products having physiological activities. LF-matters treated by heating can be dried to obtain powdery products. In this connection, any conventional drying methods can be adopted as long as the LF is not further denaturated. Typical drying methods are vacuum drying, freeze drying, spray drying and the like.

It will be understood that the resultant LF-matters, treated by heating, can be used, as is, as foods, feeds, cosmetics, medicines and the like depending upon other ingredients contained therein and can be added to fresh or processed foods or feeds, or materials thereof as well as medicines or cosmetics or materials thereof.

Now some exemplifying tests will be described for a better understanding of the present invention.

the same will be applied unless specifically noted)), the resultant solution was distributed by 10 ml into 66 test tubes. The LF solution in various test tubes was adjusted to a pH of 1–11, as shown in Table 1 to prepare samples of 11 groups each consisting of 6 samples having the same pH value. The six samples belonging to each group were heated at 6 different temperatures, 60° C.–120° C. for 5 minutes, as shown in Table 1.

After heating, appearance of the samples was observed by the naked eye to find coagulation of LF, then degree of denaturation of LF in each sample was measured by reversed-phase high performance liquid chromatography using Asahi-Pack C4P-50 (trademark, by Asahi Kasei) with linear gradient of acetonitrile containing 0.5M sodium chloride.

2) RESULTS

The results are shown in Table 1. The values in Table 1 denote undenaturation rates, i.e. the value of 100% means that LF is not denaturated. It will be understood that LF is very stable to heating under acidic conditions. Also it will be noted that there are remarkable gaps between undenaturation rates of samples of pH 6 and 7 heated at 80° C., those of samples of pH 6 and 7 heated at 90° C., and those of samples of pH 5 and 6 heated at 100° C. In order to interpolate the values between the gaps and to find preferable conditions of heat treatment under practical temperatures, similar tests were carried out on the samples having smaller difference of pH values. More particularly, samples of pH 6.5 were heated at 80° C. and 90° C., and a sample of pH 5.5 was heated at 100° C. for 5 minutes respectively. As the results, undenaturation rates thereof were 67.3% (sample of pH 6.5 heated at 80° C.), 45.0% (sample of pH 6.5 heated at 90° C.) and 63.4% (sample of pH 5.5 heated at 100° C.) respectively.

It was confirmed that the preferable combinations of heating temperature and pH value at which an undenaturation rate over 60% was resulted were: at 60° C. under pH 8 or less, at 70° C. under pH 7 or less, at 80° C. under pH 6.5 or less, at 90° C. under pH 6.0 or less, and at 100° C. under pH 5.5 or less.

TABLE 1

| Temp. (°C.) | Test Item | pH of LF Solution | | | | | | | | | | |
|---|---|---|---|---|---|---|---|---|---|---|---|---|
| | | 1 | 2 | 3 | 4 | 5 | 6 | 7 | 8 | 9 | 10 | 11 |
| 60 | coagul. | — | — | — | — | — | — | — | — | ± | ± | — |
| | undenatur. | 91.2 | 100 | 100 | 100 | 100 | 100 | 100 | 70.4 | 35.5 | 19.7 | 9.8 |
| 70 | coagul. | — | — | — | — | — | — | — | ± | ± | ± | — |
| | undenatur. | 87.5 | 100 | 100 | 100 | 100 | 100 | 100 | 51.3 | 24.1 | 10.0 | 0 |
| 80 | coagul. | — | — | — | — | — | — | — | ± | + | ± | — |
| | undenatur. | 71.1 | 93.5 | 100 | 100 | 100 | 100 | 26.8 | 12.1 | x | 0 | 0 |
| 90 | coagul. | — | — | — | — | — | — | ± | + | + | ± | — |
| | undenatur. | 50.7 | 80.4 | 93.5 | 100 | 100 | 95.7 | 15.2 | x | x | 0 | 0 |
| 100 | coagul. | — | — | — | — | — | ± | + | + | + | + | — |
| | undenatur. | 14.4 | 25.7 | 45.6 | 100 | 95.8 | 5.3 | x | x | x | x | 0 |
| 120 | coagul. | — | — | — | — | — | + | + | + | + | + | — |
| | undenatur. | 0 | 0 | 0 | 0 | 0 | x | x | x | x | x | 0 |

Note: observation by naked eye:
+: completely coagulated
±: not coagulated but semitransparent
—: not coagulated and transparent
undenaturation rate by liquid chromatography:
numerical values: percentage of peak of heated LF to peak of unheated LF in chromatogram
x: unmeasurable due to coagulation

TEST 1

The purpose of this test is to exemplify the relationship between the conditions of heat treatment and the affect on physiological activities of LF.

1) METHOD

Commercial LF (by Oleofina, Belgium) was dissolved in purified water (5% concentration (by weight,

TEST 2

The purpose of this test is to determine proper combinations of heating temperature and heating time at different pH values for achieving an undenaturation rate over 60%.

1) METHOD

Nine groups of samples of LF solutions having different pH values, 1.0, 2.0, 3.0, 4.0, 5.0, 6.0, 6.5, 7.0, and 8.0 were prepared in the same manner as in Test 1. The resultant solutions were heated at a temperature between 60° C.–120° C. for 100 minutes. Undenaturation rate was measured for each of the samples in the same manner as in Test 1, using a portion thereof which was periodically taken out and cooled. Intervals for taking out respective portions of samples were 30 seconds during 1–10 minutes after initiation of heating, 1 minute during 10–20 minutes, and 10 minutes during 20–100 minutes after initiation of heating.

2) RESULTS

The results are shown in FIG. 1 wherein combinations of heating temperature and heating time with which 60% of undenaturation rate were resulted were plotted with respect to each of the samples of pH 1.0 represented by the line x—x, of pH 2.0 represented by △—△, of pH 3.0 represented by □—□, of pH 4.0 represented by ○—○, of pH 5.0 represented by ●—●, of pH 6.0 represented by ▲—▲, of pH 6.5 represented by ⊖—⊖, of ph 7.0 represented by ■—■, and of pH 8.0 represented by ♦—♦, and wherein the ordinate shows heating time in logarithmic graduation and the abscissa shows heating temperature.

Any combinations of temperature and time in the regions below the respective lines in FIG. 1, may result in undenaturation rate over 60% for respective LF-matters having the corresponding pH.

It was confirmed that LF-matters are stable under acidic pH condition between 1.0–6.5, especially between 2.0–6.0 and that even if LF-matters are heated at a relatively higher temperature, denaturation of LF can be kept at relatively low degree, if the heating time is shortened. For example, when an LF-matter of pH 4.0 is heated at 120° C., undenaturation rate over 60% can be resulted by restricting the heating time for 3 minutes or less, though the undenaturation rate was 0% when the LF-matter is heated at 120° C. for 5 minutes (cf. Table 1). It will be understood that when an LF-matter of pH 2.0 is heated at 100° C. for 5 minutes, the undenaturation rate was lower than 60% (25.7% in Table 1), however, an undenaturation rate over 60% can result if heating time is less than 2 minutes (cf. FIG. 1).

It will be understood that in order to achieve an undenaturation rate over 60%, any combination of a heating temperature, a heating time and a pH value can be selected in the region below the line corresponding to the adopted pH value of an LF-matter taking the purpose of heat treatment in consideration.

TEST 3

The purpose of this test is to determine the effect of heat treatment of LF on antibacterial activity.

1) METHOD

1-1) PREPARATION OF CULTURE MEDIUM AND PRE-CULTURE

1-1-1) PREPARATION OF PRE-CULTURE

From the stock culture of *Escherichia coli*, bacterial cells was taken out with a platinum loop and spread onto a plate count agar (by Nissui Seiyaku), followed by stationary incubation at 35° C. for 16 hours (under aerobic condition). The colonies grown on the surface of the culture were collected with a platinum loop and suspended into pasteurized physiological saline solution to prepare pre-culture having optical density of 1.0 (at 660 nm) measured by a spectrophotometer (by Hitachi Seisakusho).

1-1-2) PREPARATION OF BASIC CULTURE MEDIUM

Basic culture medium (liquid culture medium) was prepared by dissolving bactocasitone (by Difco) into purified water in 1% concentration, adjusting the pH of the resultant solution to 7.0 by 1M sodium hydroxide, and then pasteurizing at 115° C. for 15 minutes.

1-1-3) PREPARATION OF TEST CULTURE MEDIUM

LF solution adjusted to pH 4.0 was heated (for pasteurization) at 100° C. for 5 minutes in the same manner as in Test 1 to prepare a test sample of heated LF solution. A quantity of the resultant heated LF solution was added to a portion of the basic culture medium to prepare a test culture medium containing 1,000 ppm of heated LF.

LF solution adjusted to pH 4.0 was filtrated with a membrane filter (by Advantec) to remove any microbial cells contaminated therein to prepare unheated LF solution. A quantity of the resultant unheated LF solution was added to a portion of the basic culture medium to prepare a test culture medium containing 1,000 ppm of unheated LF.

1-1-4) PREPARATION OF CONTROL CULTURE MEDIUM

Sterilized water of the same quantity to that of LF solutions for preparing test culture media was added to a portion of the basic culture medium to prepare a control culture medium containing no LF.

1-2) TEST FOR ANTIBACTERIAL ACTIVITY

To each of the test and control culture medium, the pre-culture was inoculated in 1% concentration, followed by incubation at 35° C. for 15 hours. The growth inhibition rate was determined by periodically measuring optical density of the culture broths after 5, 10 and 15 hours from the initiation of incubation in the same manner as previously described and calculated in accordance with the following formula.

growth inhibition rate $(\%) = 100 - (A/B \times 100)$
(wherein A denotes the difference of the respective optical densities of the test culture medium after 5, 10 and 15 hours incubation and that of before incubation, B denotes the difference of the respective optical densities of the control culture medium after 5, 10 and 15 hours incubation and that of before incubation respectively)

In preparation of test and control culture medium, there were no substantial changes in pH values before and after addition of LF solutions or sterilized water to the basic culture medium.

2) RESULTS

The results are shown in Table 2. It was confirmed that antibacterial activity of heated LF and unheated LF was almost the same.

TABLE 2

| Sample | Proliferation Inhibition Rate (%) | | |
|---|---|---|---|
| | after 5 hrs | after 10 hrs | after 15 hrs |
| Control | 0 | 0 | 0 |
| unheated LF | 28.3 | 7.0 | 1.0 |
| heated LF | 23.3 | 9.9 | 1.2 |

TEST 4

The purpose of this test is to determine the effect of heat treatment of LF on the iron binding property.

1) METHOD

Heated LF solution (pH 4.0, heated at 100° C. for 5 minutes) and unheated LF solution were prepared in the same manner as in Test 3. The iron binding property of the resultant LF solutions were measured by the method of Baer et al (A. Baer et al, Journal of Dairy Research, Vol. 46, page 83, 1979), and the percentage of the quantity of iron bound to heated LF to the quantity of iron bound to unheated LF was calculated.

2) RESULTS

The results are shown in Table 3. Iron binding property of heated LF and unheated LF is almost the same, and found that there is no substantial effect on the iron binding property of LF by heat treatment.

TABLE 3

| Sample | Iron Binding Property |
|---|---|
| unheated LF | 100% |
| heated LF | 97% |

TEST 5

The purpose of this test is to determine the effect of heat treatment on the antigenicity of LF.

1) METHOD

Antigenicity of samples of heated LF and unheated LF prepared in the same manner as in Test 4 (pH 4.0, heated at 100° C. for 5 minutes) were measured by Laurell's method (C. B. Laurell, Analytical Biochemistry, Vol. 15, page 45, 1966), and the percentage of the value of antigenicity of heated LF to that of unheated LF was calculated.

2) RESULTS

The results are shown in Table 4. It was confirmed that antigenicity of heated LF is almost the same with that of unheated LF, and there is no substantial difference therebetween.

TABLE 4

| Sample | Antigenicity (%) |
|---|---|
| unheated LF | 100 |
| heated LF | 99 |

TEST 6

The purpose of this test is to exemplify the antibacterial activity of heated LF when it was added to milk.

To 10 kg of sterilized milk (sterilized at 70° C. for 30 minutes then cooled), 500 g of heated LF solution (conditions of heat treatment: pH 5.0, at 70° C., for 30 minutes) was aseptically added to prepare a test sample (Sample No. 1). The resultant test sample was distributed into bottles by 200 ml and sealed. A control sample (Sample No. 2) which consisting of sterilized milk to which no LF was added (conditions of sterilization is the same with that of the milk used in preparation of test sample No. 1) and a control sample (Sample No. 3) which consists of sterilized milk (conditions of sterilization is the same with that of the milk used in preparation of test sample No. 1) and sterilized LF (deactivated) in the milk (concentration of LF is the same with that in Sample No. 1) were prepared.

The resulted samples were preserved at 25° C. to observe any change in appearance with the naked eye to determine the activity of the added LF.

All of the Sample Nos. 2 and 3 were coagulated by the 2nd day from the initiation of preservation, whereas there was observed no coagulation in Sample No. 1 by the 5th day from the initiation of preservation.

It will be understood that coagulation of milk means acidification or fermentation of milk. From the results, it was confirmed that antibacterial activity of LF heated in accordance with the present invention is effective for preservation of milk. The results of this test make it possible to assume that LF heated in accordance with the present invention is effective also for preservation of any and all matters other than milk when the heated LF is added in the same manner thereto. It is also apparent that other physiological activities of the heated LF exemplified by the previous tests are maintained in the test sample (Sample No. 1).

Now, some examples will be described for better understanding of the present invention.

EXAMPLE 1

To 29.7 kg of purified water, 300 g of commercial LF (by Oleofina, Belgium) was dissolved, then the pH of the resultant solution was adjusted to 4.0 with 1M hydrochloric acid. The resultant solution was preheated at 70° C. for 3 minutes, then sterilized at 130° C. for 2 seconds using UHT sterilization system (by Morinaga Engineering), followed by cooling to 15° C., thereby about 30 kg of heated LF solution was obtained.

The undenaturation rate of the resultant LF solution was 99% as measured by the same method as in Test 1 (liquid chromatography). There was no scorching and no sticking of LF to sterilization system during the heat treatment. The resultant LF solution can be used as it is as a medicine and can be used as an ingredient of pharmaceutical preparations or cosmetics and can be used as an additive for foods or feeds.

EXAMPLE 2

To 20 kg of orange juice having the ingredient as shown in Table 5, 1 kg of commercial LF (by Oleofina, Belgium) was dissolved. The resultant solution was heated at 80° C. for 15 minutes, followed by cooling, asepticaly distributed into glass bottles by 200 ml, sealed, thereby 95 bottles of orange juice were produced. The undenaturation rate of the heated LF in the orange juice was 99.6% as measured by the same method as in Test 1 (liquid chromatography).

TABLE 5

| sugar | 5.0% |
|---|---|
| perfume (orange) | 0.2% |
| citric acid | 0.1% |
| sodium citrate | 0.05% |
| carbonated water | 94.65% |
| Total | 100 |

Notes:
nature of the mixture: pH 4.5, liquid, transparent and orange in color

EXAMPLE 3

To 9.5 kg of purified water, 500 g of commercial LF (by Oleofina, Belgium) was dissolved. The resultant solution was adjusted to pH 5.0 with 1M citric acid. The resultant solution was heated at 70° C. for 30 minutes, followed by cooling, thereby about 10 kg of heated LF solution was obtained.

EXAMPLE 4

A mixture of

| salad oil | 6.8 kg |
|---|---|
| vinear | 1.4 kg |
| lemon juice | 0.13 kg |

-continued

| egg yolk | 1.37 kg |
|---|---|
| table salt | 0.06 kg |
| sugar | 0.14 kg |
| mustard | 0.10 kg |
| commercial LF | 0.1 kg (by Oleofina, Belgium) | was sufficiently stirred, then resulted mixture was heated at 60° C. for 10 minutes under stirring, followed by cooling, thereby about 10 kg of mayonnaise (pH 4.0) containing heated LF was obtained.

EXAMPLE 5

A mixture of

| water | 2.9 kg |
|---|---|
| commercial apple juice | 0.75 kg |
| powdery agar | 0.05 kg |
| granulated sugar | 2.05 kg |
| commercial LF (by Oleofina, Belgium) | 50 g | was homogeneously mixed, the resulted mixture (pH 5.0) was heated at 90° C. for 20 minutes, the resultant solution was poured into a flat pan, followed by cooling. Resultant gel was cut into 2 cm cubes, followed by drying on a mesh, sprinkled with granulated sugar, thereby 500 pieces of jelly containing heated LF were produced.

EXAMPLE 6

In a column having 10 cm diameter, 500 ml of ion-exchange resin, CM-Toyopearl 650C (trademark, by TOSOH) was filled, followed by passing 2 l of 10% NaCl solution into the column, washing by water, thereby Na type ion-exchange column was prepared. To the resultant column, 60 l of goat cheese whey (pH 6.5) was passed at the flow rate of 4 l/h at 4° C. The components adsorbed to the resin were eluted by the conventional procedures to thereby obtained about 5 l of the eluate. The resultant eluate was dialyzed against purified water, followed by ultrafiltration with an ultrafiltration module SEP-1013 (by Asahi Kasei) to concentrate the eluate, to thereby obtain about 200 ml of 1% goat LF solution.

The resultant LF solution was adjusted to pH 4.0 by adding 1M hydrochloric acid, followed by heating at 80° C. for 15 minutes, cooling to 15° C., to thereby obtain about 200 ml of heated goat LF solution.

The undenaturation rate of the LF contained in the solution was 99.7% as measured by the same method as in Test 1 (liquid chromatography).

EFFECTS OF THE INVENTION

The effects of the present invention are as follows:

1) Heated LF prepared by the present invention can be safely used for foods, feeds, medicines and cosmetics, since it is a natural substance which is included in milk.

2) The method of the present invention is suitable to be applied for preparation and processing, involving heat treatment, of foods, feeds, medicines and cosmetics containing LF.

3) Any matters which contain LF can be sterilized, pasteurized or cooked by heating without affecting physiological activities of LF.

What is claimed is:

1. A method for treatment of a matter which contains moisturized or liquified lactoferrin which has been isolated from mammalian milk or processed mammalian milk, without losing the physiological activities of lactoferrin which comprises:
   a) adjusting pH of said moisturized or liquified lactoferrin contained in said matter to within an acetic pH range of between 2.0 and 6.0 both inclusive by adding acid or aqueous solution of acid thereto when the pH of said moisturized or liquified lactoferrin is out of said pH range; and
   b) heating said matter under a combination of a temperature between 60° C.–130° C., time between 400 minutes–2 seconds, and, the adjusted pH of said matter to result in sterilization and an undenaturation rate of lactoferrin of not less that 60%.

2. A method for treatment of a matter which contains moisturized or liquified lactoferrin, without losing the physiological activities of lactoferrin which comprises:
   a) adjusting pH of said moisturized or liquified lactoferrin contained in said matter to within an acetic pH range of between 2.0 and 6.0 both inclusive by adding acid or aqueous solution of acid thereto when the pH of said moisturized or liquified lactoferrin is out of said pH range; and
   b) heating said matter under a combination of a temperature between 60° C.–130° C., time between 400 minutes–2 seconds, and, the adjusted pH of said matter to result in sterilization and an undenaturation rate of lactoferrin of not less than 60%.

* * * * *